United States Patent
Hall et al.

(10) Patent No.: US 10,126,274 B2
(45) Date of Patent: Nov. 13, 2018

(54) METHOD AND SYSTEM FOR MULTI-PATH ACTIVE DEFECT DETECTION, LOCALIZATION AND CHARACTERIZATION WITH ULTRASONIC GUIDED WAVES

(71) Applicant: HIDDEN SOLUTIONS, LLC, Kissimmee, FL (US)

(72) Inventors: James Stroman Hall, Kissimmee, FL (US); Jennifer Emmons Michaels, Tucker, GA (US)

(73) Assignee: HIDDEN SOLUTIONS LLC, Orlando, FL (US)

( * ) Notice: Subject to any disclaimer, the term of this patent is extended or adjusted under 35 U.S.C. 154(b) by 624 days.

(21) Appl. No.: 14/396,373

(22) PCT Filed: Jan. 25, 2013

(86) PCT No.: PCT/US2013/023225
§ 371 (c)(1),
(2) Date: Oct. 22, 2014

(87) PCT Pub. No.: WO2013/172876
PCT Pub. Date: Nov. 21, 2013

(65) Prior Publication Data
US 2015/0160169 A1  Jun. 11, 2015

(51) Int. Cl.
G01N 29/44 (2006.01)
G01N 29/04 (2006.01)
G01M 7/02 (2006.01)
G01N 29/24 (2006.01)

(52) U.S. Cl.
CPC ............. *G01N 29/44* (2013.01); *G01M 7/02* (2013.01); *G01N 29/04* (2013.01); *G01N 29/2475* (2013.01); *G01N 29/449* (2013.01); *G01N 29/4418* (2013.01); *G01N 29/4472* (2013.01); *G01N 2291/0231* (2013.01); *G01N 2291/0234* (2013.01); *G01N 2291/0258* (2013.01); *G01N 2291/0289* (2013.01); *G01N 2291/0425* (2013.01); *G01N 2291/106* (2013.01); *G01N 2291/2694* (2013.01)

(58) Field of Classification Search
USPC ............................................. 73/632; 600/443
See application file for complete search history.

(56) References Cited

U.S. PATENT DOCUMENTS

| | | | | |
|---|---|---|---|---|
| 2009/0133501 A1* | 5/2009 | Georgeson | ............. | G01N 29/04 73/632 |
| 2011/0112404 A1* | 5/2011 | Gourevitch | ............. | A61B 5/417 600/443 |

* cited by examiner

*Primary Examiner* — Lam Nguyen
(74) *Attorney, Agent, or Firm* — William Lovin & Assoc., LLC; William R. Lovin

(57) ABSTRACT

A method and system of detecting, localizing, and characterizing a defect at one or more spatial points of interest on a structure. The method may include collecting first data in a first state using one or more transducers on the structure, collecting second data in a second state subsequent to the first state, computing a scattered impulse response based on the collected first data and the collected second data, comparing the scattered impulse response with an estimated scattered impulse response corresponding to the case when damage is present at one or more spatial points of interest on the structure, and combining the generated comparison results to detect, localize, and characterize a defect at the one or more spatial points of interest on the structure.

20 Claims, 9 Drawing Sheets

METHOD AND SYSTEM FOR MULTI-PATH ACTIVE DEFECT DETECTION, LOCALIZATION AND CHARACTERIZATION WITH ULTRASONIC GUIDED WAVES

STATEMENT REGARDING FEDERALLY SPONSORED RESEARCH OR DEVELOPMENT

This invention was made with government support under Grant No. NNX12CF12P, awarded by the United States National Aeronautics and Space Administration (NASA). The government has certain rights in the invention.

CROSS-REFERENCE TO RELATED APPLICATIONS

This application claims the priority benefit of U.S. Provisional Application No. 61/647,762, filed May 16, 2012, and U.S. Provisional Application No. 61/756,452, filed Jan. 24, 2013, the entireties of which are hereby incorporated by reference.

BACKGROUND

1. Field of Invention

The invention relates generally to methods and systems for nondestructive evaluation and/or structural health monitoring and, more particularly, to a method and system for multi-path active defect detection, localization, and characterization using ultrasonic guided waves.

2. Discussion of Related Art

There is a well-recognized need for rapid and reliable methods to inspect large-area plate-like structures such as, for example, metallic and composite aerospace components, marine vessel hulls, and civil, nuclear, and petrochemical infrastructure. Ultrasonic guided waves have been identified and utilized for this purpose because they travel for long distances in the plane of the structure and are sensitive to both surface and sub-surface features.

Several known methods have been developed to perform nondestructive evaluation (NDE) and/or structural health monitoring (SHM) utilizing ultrasonic guided waves. Known elliptical and hyperbolic methods, for example, use time-of-arrival or time-difference-of-arrival information, respectively, to identify elastic scattering from defects or damage. For example, C. H. Wang, J. T. Rose, and F.-K. Chang, "A synthetic time-reversal imaging method for structural health monitoring," *Smart Materials and Structures*, 13 (2), pp. 415-423 (2004) and J. E. Michaels, A. J. Croxford, and P. D. Wilcox, "Imaging algorithms for locating damage via in situ ultrasonic sensors," in *IEEE Sensors Applications Symposium*, pp. 63-67 (2008), both of which are hereby incorporated by reference. Alternatively, as disclosed, for example, in P. Malinowski, T. Wandowski, I. Trendafilova, and W. Ostachowicz, "A phased array-based method for damage detection and localization in thin plates," *Structural Health Monitoring*, 8 (1), pp. 5-15 (2009), hereby incorporated by reference, phased arrays have been shown to identify scatterers using beamforming techniques.

A common characteristic among most known methods developed to date is that they inherently assume a homogeneous, isotropic medium with a clear, direct path between the transducers and the interrogation structure. To balance the needs of weight, function, and cost, however, practical large-area structures are increasingly being constructed of inhomogeneous or anisotropic materials and often contain a large number of structural features such as, for example, stiffeners, ribs, cut-outs, fasteners and the like. Consequently, the underlying assumptions of state-of-the-art ultrasonic guided wave defect detection and localization algorithms are no longer practical assumptions.

In complex structures, guided waves often travel along indirect paths and via multiple modes between transmitter and receiver. If damage is introduced in such a structure, signal changes caused by the damage may be readily observed, but with existing methods it can be impossible to relate the changes to a specific location, or determine the type and severity of the damage. A known approach involves high sensor density in an attempt to ensure that there are sufficient direct paths between transducers and every location of interest on the structure that pass through an essentially homogeneous material. While such an approach may be technically viable, it is usually not economically viable because of the added cost and weight. A further complication is the impracticality of directly modeling ultrasonic waves propagating in a truly complex structure. Even if modeling were practical, unavoidable deviations between the as-built and modeled structures prohibit direct comparisons of modeled data with actual measurements.

SUMMARY

A method and system, including an apparatus and/or software, for detecting, locating, and/or characterizing a mechanical feature using a spatially distributed array of transducers may be provided. The method and system may be applicable to the use of a small number of transducers to inspect large, complex structures for the purpose of long-term nondestructive evaluation or structural health monitoring. Embodiments of the invention may be based on two basic concepts: (1) estimating the combined transducer transfer functions and spatial Green's function of a potential scatterer located at a spatial point of interest, and (2) combining these estimates with data recorded from the spatially distributed array to detect, locate, and characterize scatterers in the structure.

According to an embodiment of the invention, a method and system may be provided to detect, locate, and/or characterize defects or damage in a large, complex, plate-like structure using a distributed array of sensors. The method and system may leverage the multi-path reverberations and echoes that are produced by complex structures to provide improved defect detection and localization capabilities with fewer sensors than prior art. This may be accomplished by estimating the changes that will be observed by the distributed array should damage be introduced in the structure, and then quantitatively comparing the estimated changes to those measured from the structure while in service.

According to an embodiment, the method and system may estimate the signal changes that will result in the event of damage. A single estimate, for example, may be constructed by (1) exciting a guided wave using one of the spatially distributed array sensors, (2) measuring the response of the structure to the source excitation at a potential defect location, (3) exciting a second guided wave using a second array sensor, (4) measuring the response of the structure to the second excitation at the same potential defect location, and (5) combining the two measurements. This approach may leverage the reciprocal nature of transducers such as, for example but not limited to, piezoelectric transducers, and may provide an ability to obtain consistent estimates of anticipated signal changes as a result of damage to the structure. Furthermore, the method and system may assist in efficiently obtaining these signal change estimates for a large number of potential defect locations through the use of a movable sensor, such as a scanning laser vibrometer (SLV) or scanned air-coupled ultrasonic transducer (SAUT).

In an embodiment of the invention, a method of estimating a scattered impulse response at one or more spatial points of interest on a structure may be provided. The method may include collecting data at the one or more spatial points of interest on the structure using a movable transducer. The data collection may include individually exciting at least one transducer on the structure with a known excitation function and recording measurements with the movable transducer. The method may include computing an estimated scattered impulse response at the one or more spatial points of interest based on the collected data. The collected data may include mode and/or directional specificity.

In an embodiment of the invention, a method and system of detecting, localizing, and characterizing a defect at one or more spatial points of interest on a structure are provided. The method may include providing an estimated scattered impulse response at the one or more spatial points of interest, collecting first data in a first state from at least one transducer on the structure, and collecting second data from the at least one transducer on the structure in a second state subsequent to the first state. The collecting first data may include individually exciting the at least one transducer with a known excitation function and recording a signal received at the at least one transducer. The collecting second data in the second state may include individually exciting the at least one transducer with a known excitation function and recording a signal received at the at least one transducer. The method may include computing a scattered impulse response based on the collected first data and the collected second data, comparing the estimated scattered impulse response with the scattered impulse response to generate comparison results, and combining the generated comparison results to detect, localize, and characterize a defect at the one or more spatial points of interest on the structure.

According to an embodiment, a system for detecting, localizing, and characterizing a defect at one or more spatial points of interest on a structure may be provided. The system may include at least one transducer on the structure, a storage device containing an estimated scattered impulse response for one or more spatial points of interest on the structure, and a processor coupled to the at least one transducer. The at least one transducer may be configured to be excited according to a known excitation function and to record a signal received from excitation of the at least one transducer. The processor may be configured to: collect first data in a first state by processing the signal received at the at least one transducer; collect second data from the plurality of transducers in a second state subsequent to the first state by individually exciting the at least one transducer with the known excitation function and processing a signal received at the at least one transducer; compute a scattered impulse response based on the collected first data and the collected second data; compare the scattered impulse response with the estimated scattered impulse response to generate comparison results; and combine the generated comparison results to detect, localize, and characterize a defect at the one or more spatial points of interest on the structure.

According to yet another embodiment, the method and system may characterize the likelihood that a defect is located at any of a number of potential defect locations. For each potential defect location, scattered array signals measured from the structure while in service can be compared to scattered array signal estimates through cross-correlation, deconvolution, or a modification of one or both of these functions, such as, for example, Weiner deconvolution. This approach to localization may leverage the multi-path echoes and variations in propagation velocity that are inherent in complex structures and may offer substantial improvements over conventional active interrogation techniques. The relative likelihood for each of the potential defect locations can either be presented as an image to facilitate interpretation and localization, or interpreted directly for automated damage detection and localization.

Further features and advantages, as well as the structure and operation of various embodiments of the invention, are described in detail below with reference to the accompanying drawings.

BRIEF DESCRIPTION OF THE DRAWINGS

The foregoing and other features and advantages of the invention will be apparent from the following, more particular description of some example embodiments of the invention, as illustrated in the accompanying drawings. Unless otherwise indicated, the accompanying drawing figures are not to scale. Several embodiments of the invention will be described with respect to the following drawings, in which like reference numerals represent like features throughout the figures, and in which.

DETAILED DESCRIPTION

Some embodiments of the invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the invention. All references cited herein are incorporated by reference as if each had been individually incorporated.

Figure 1:
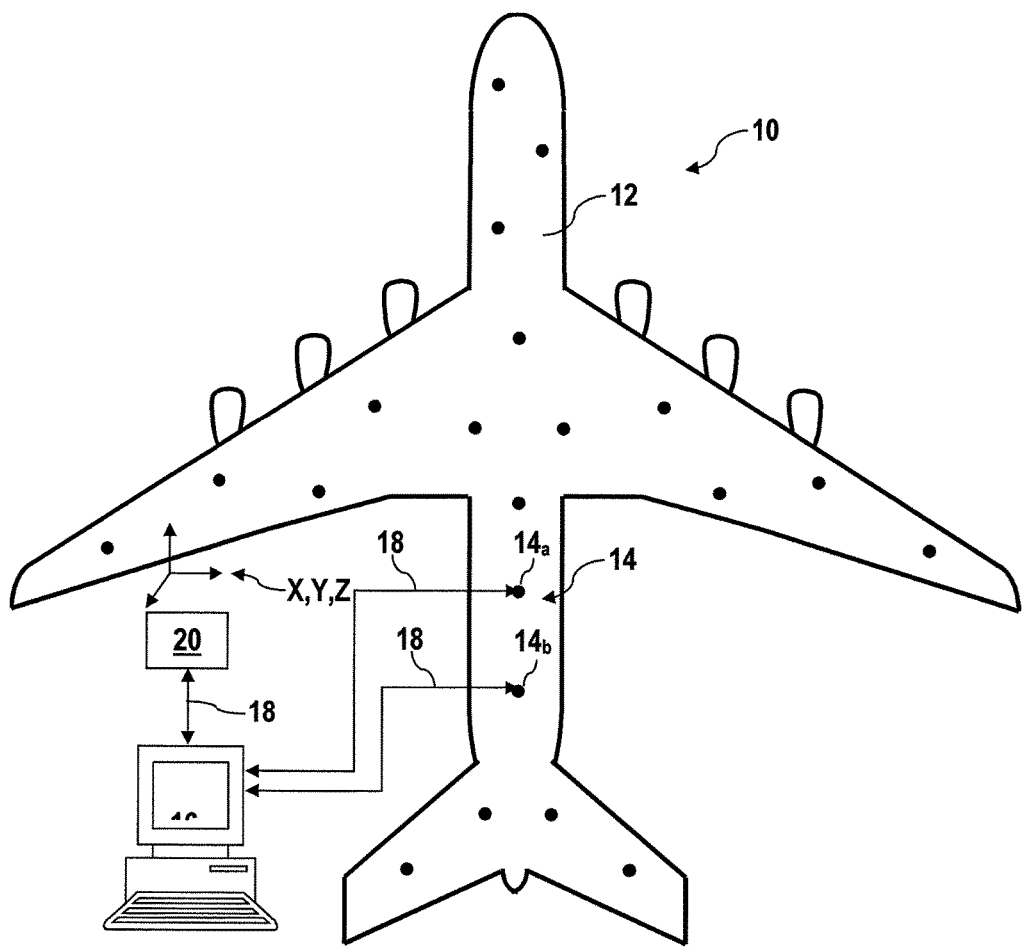
FIG. 1 is a schematic representation of a spatially distributed array of transducers mounted on an aircraft structure illustrating a potential practical application of the system and method for multi-path active defect detection, localization, and characterization with ultrasonic guided waves according to an embodiment of the invention.

FIG. 1 is a schematic representation of a system 10 for multi-path active defect detection, localization, and/or characterization with ultrasonic guided waves according to an embodiment of the invention. As shown in FIG. 1, the system 10 may include a spatially distributed array 14 of transducers 14a, 14b, etc., mounted on a structure 12 such as, for example but not limited to, an aircraft structure. Other structures may include, for example, metallic and composite aerospace components, marine vessel hulls, as well as civil, nuclear, and petrochemical infrastructure. Each transducer 14a, 14b, etc. may be coupled via a communication link 18 to a computer 16 having a processor. A movable transducer 20 may also be provided for taking and recording measurements at one or more spatial points of interest on the structure 12. The movable transducer 20 may be a non-contact vibration measurement device or sensor arranged to be moved in one or more dimensions along axes X, Y, Z as shown schematically in FIG. 1. The movable transducer 20 may be coupled via a communication link 18 to the computer 16. Computer 16 may transmit instructions to and receive data from the array 14 and the movable transducer 20 via communication links 18 which may be wired or wireless.

In the embodiment depicted in FIG. 1, the spatially distributed array 14 may be permanently attached on the aircraft structure 12. The location of each transducer 14a, 14b, etc. may be prescribed or arbitrary; there are, however, no restrictions regarding an array pattern or proximity to structural features or other transducers. It is understood that there is a sufficient number of transducers 14 distributed throughout the structure 12 so that all locations of interest (e.g., potential damage locations) are appropriately insonified. In the embodiment of FIG. 1, each transducer 14a, 14b, etc. in the spatially distributed array 14 may be, for example but not limited to, an inexpensive piezoelectric transducer which may be permanently attached to the structure 12, either through adhesive bonding or embedding the sensors within the structure 12 itself. The distributed array 14 need not be permanently attached to the structure 12. The transduction mechanism of transducer 14a, 14b, etc., may or may not be piezoelectric in nature.

Figure 2:
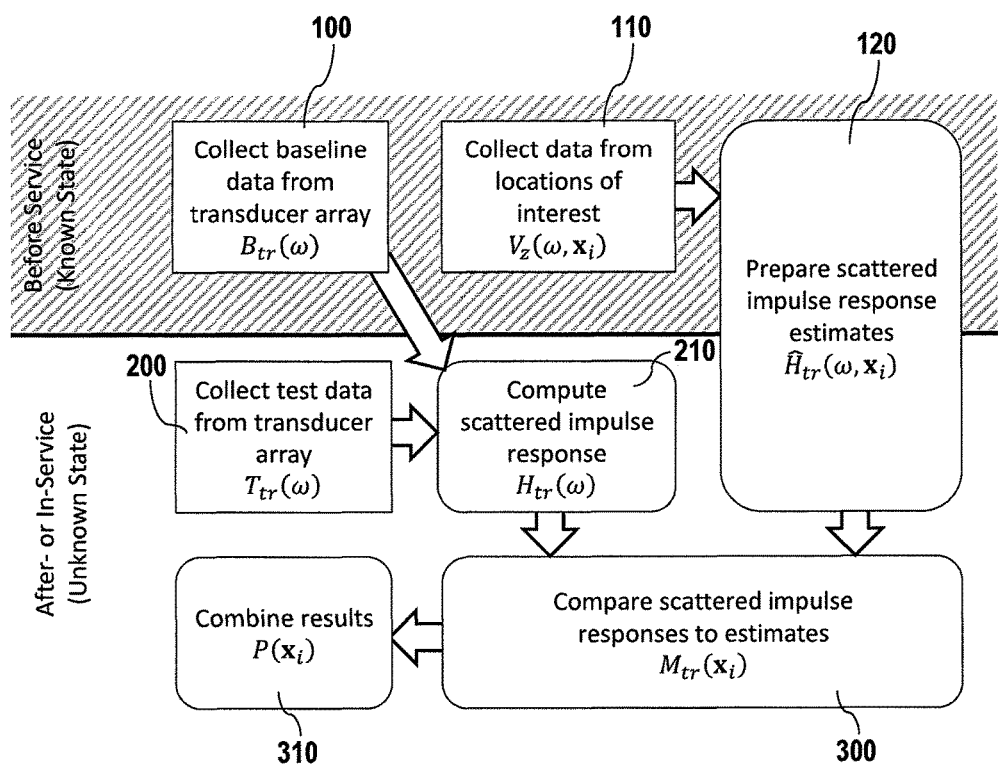
FIG. 2 illustrates a flow chart depicting a method of detecting, localizing, and characterizing a defect at one or more spatial points of interest on a structure according to an embodiment of the invention.

FIG. 2 illustrates a flow chart depicting a method of detecting, localizing, and characterizing a defect at one or more spatial points of interest on a structure 12 according to an embodiment of the invention. The method depicted in FIG. 2 may, for example, be carried out utilizing the system 10 described above and shown in FIG. 1. The flow chart in FIG. 2 is understood to outline the steps of the method for the case of a single propagating mode and a point-like scatterer. In FIG. 2, boxes with square corners indicate data collection/acquisition steps, while boxes with rounded corners correspond to calculation steps. The greyed area identifies data collection steps that are performed while the structure is in a known state. Steps shown outside the greyed area include those performed while the structure is in an unknown state (e.g., when the structure is placed into service). The data acquisition steps (100, 110, 200) and computation steps (120, 210, 300, 310) are described in detail below using a frequency-domain model. The use of a frequency-domain model was chosen for readibility and the concepts described herein are equally applicable to implementations using equivalent or alternative domains, such as time, spatial, or wavenumber domains.

As shown in FIG. 2, two sets of data, baseline data, $B_{tr}(\omega)$, from the transducer array 14, and measurement data, $V_z(\omega, x_i)$, from spatial locations of interest $x_i$, are collected from the structure 12 in steps 100 and 110, respectively, while the structure 12 is in a known state, e.g., before the structure 12 is put into service. In this known state, the condition of the structure 12 does not necessarily have to be damage-free, but any damage present during the collection of this data will not be detected. Step 120 is shown in a box spanning the known and unknown states because this step may be performed either before or after the structure 12 is put into service, depending on application-specific needs. It is understood, however, that the measurement data $V_z(\omega, x_i)$ correspond to the same known state as the baseline data, $B_{tr}(\omega)$.

Figure 3:
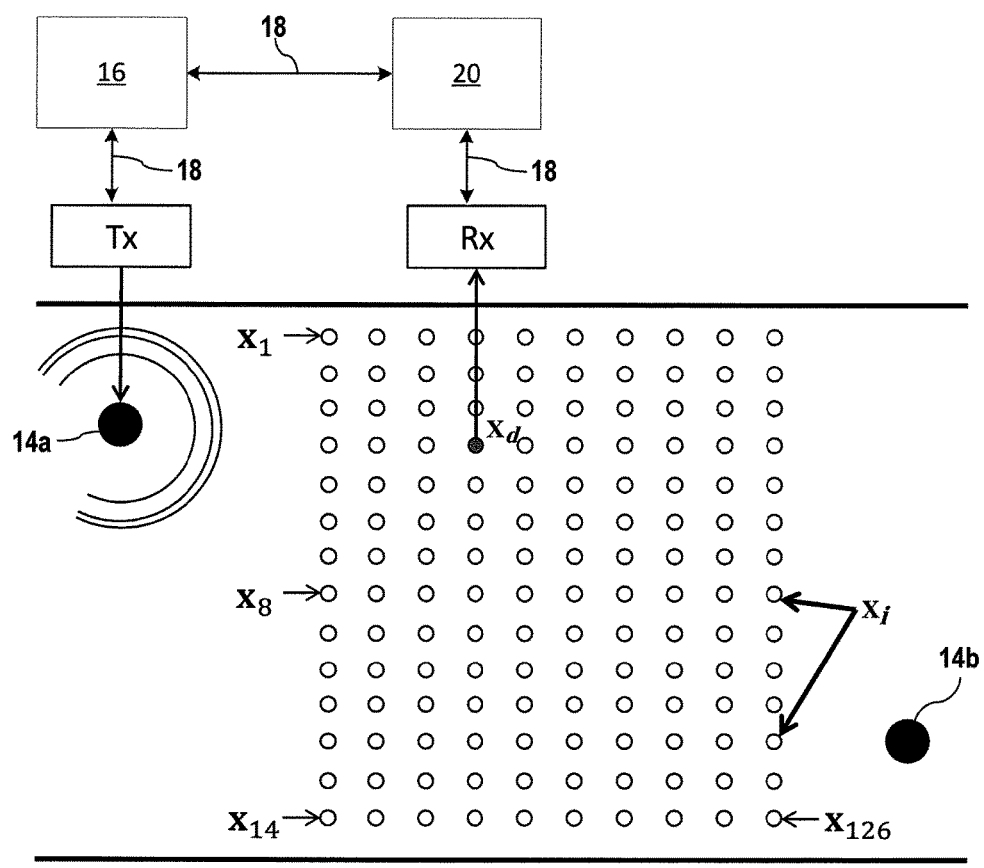
FIG. 3 is an illustrative and schematic depiction of collecting data in a first known state at the one or more spatial points of interest on the structure using a movable transducer according to an embodiment.

In step 110 in FIG. 2, data is collected from spatial locations of interest $x_i$ by the movable transducer 20 in the known state. FIG. 3, for example, graphically depicts collection of the $V_z(\omega, x_i)$ measurements (step 110). Each measurement is obtained from a location of interest, $x_i$, while a transducer z (in this case, transducer 14a) acts as a transmitter. That is, computer 16 outputs a known excitation signal Tx via communication link 18 to transducer 14a, which in turn generates mechanical (e.g., ultrasonic) waves in the structure. The movable transducer 20 may be controlled by the computer 16 to move to a desired location to take measurements at spatial point of interest $x_d$ among any number of points of interest $x_i$. Measurements can be taken by the movable transducer 20 in whatever density or pattern is desired; they need not be taken on a grid or at any specific spatial interval. The movable transducer 20 may be a sensor such as, for example but not limited to, a scanning laser vibrometer (SLV) and/or a scanning air-coupled ultrasonic transducer (SAUT), and may be used to efficiently obtain $V_z(\omega, x_i)$ measurements from one or more locations of interest on the structure.

Figure 4:
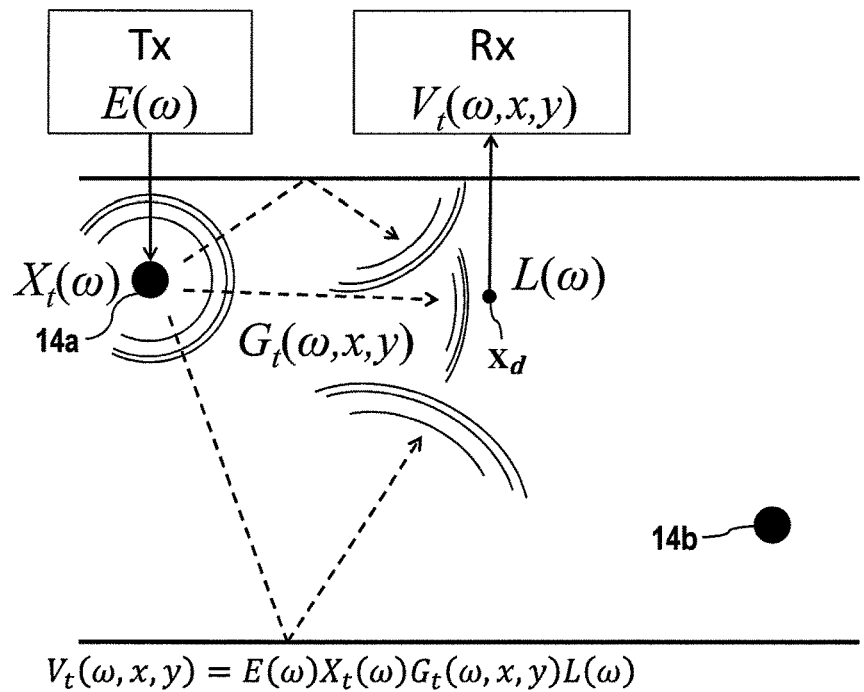
FIGS. 4 and 5 illustrate excitation of a transducer on the structure and measurement of the mechanical waves at the one or more spatial points of interest using the movable transducer according to an embodiment.
Figure 5:
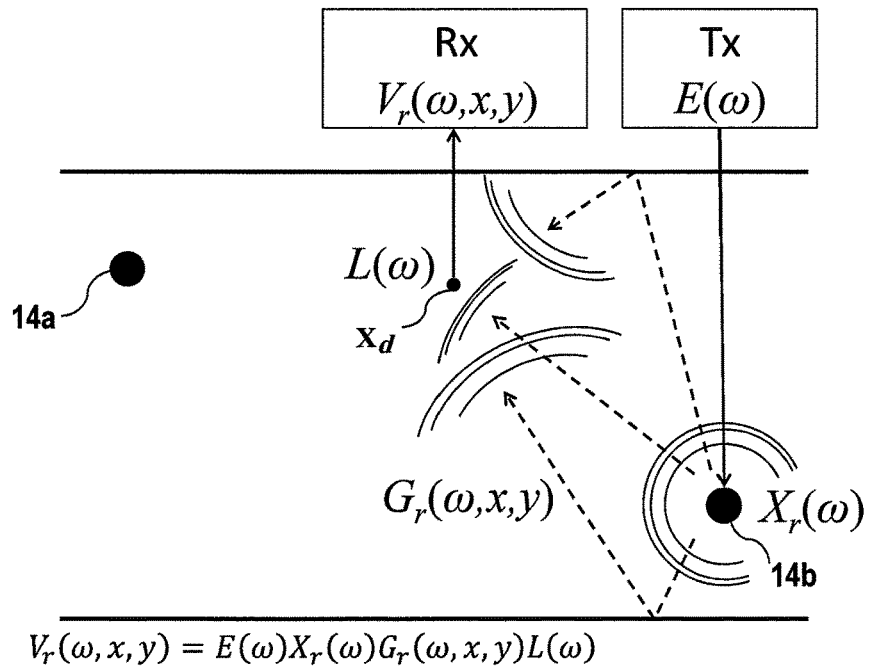

A mathematical model used to describe these $V_z(\omega, x_i)$ measurements is:

$$V_z(\omega, x_i) = E(\omega) X_z(\omega) G_z(\omega, x_i) L(\omega), \quad (1)$$

where $\omega$ is the radian frequency; $E(\omega)$ is the source function or known excitation function, corresponding to the electrical signal sent to transducer z, and is considered known in the methods and systems described herein; $X_z(\omega)$ is the transducer transfer function for transducer z, which describes the transduction from electrical to mechanical waves; $G_z(\omega, x_i)$ is the Green's function that encompass all paths from transducer z to location of interest $x_i$, including dispersion, propagation loss, and geometric scattering effects; and finally, $L(\omega)$ describes the transfer function from mechanical waves to electrical energy for the movable sensor. FIGS. 4 and 5 illustrate individual excitation of first and second transducers 14a, 14b, respectively, of the transducer array 14 on the structure 12 and measurement of the mechanical waves at the one or more spatial points of interest $x_d$ using the movable transducer 20 according to an embodiment.

As shown in step 100 in FIG. 2, baseline data, $B_{tr}(\omega)$, is collected using the spatially distributed array of transducers 14 while the structure 12 is in a known state. The t and r subscripts correspond to transmit and receive transducer indices, respectively. Data is collected by individually exciting one or more transducers in the distributed array 14, e.g., transducer 14a, and recording received signals from one or more of the remaining transducers, e.g, transducer 14b. For example, if the array 14 is comprised of N transducers, then $N^2$ possible $B_{tr}(\omega)$ signals can be obtained. It should be noted, however, the actual number of $B_{tr}(\omega)$ signals recorded and used in the algorithm is application-specific and may be substantially less than $N^2$. For example, most systems are expected to employ $N(N-1)/2$ or fewer $B_{tr}(\omega)$ signals since this is the number of unique transducer pairs. At a minimum, a single $B_{tr}(\omega)$ signal is required.

Once steps 100 and 110 of FIG. 2 are performed in the known state, test data, $T_{tr}(\omega)$, may be collected in step 200 in the same manner as the collection of baseline data $B_{tr}(\omega)$, but test data, $T_{tr}(\omega)$, may be collected after the structure 12 has been placed into service and is in an unknown, possibly damaged, condition. To isolate any echoes and reverberations corresponding to changes in the structure 12, the test data $T_{tr}(\omega)$ is compared to baseline data $B_{tr}(\omega)$ to compute scattered signals. For this embodiment, scattered signals are computed as follows:

$$S_{tr}(\omega) = T_{tr}(\omega) - B_{tr}(\omega).$$

The foregoing signal differencing may include a number of additional adaptive steps to improve signal-to-noise ratio, e.g. optimal baseline subtraction (OBS) as described, for example, in Y. Lu and J. E. Michaels, "A methodology for structural health monitoring with diffuse ultrasonic waves in the presence of temperature variations," *Ultrasonics,* 43 (9), pp. 717-731 (2005), incorporated herein by reference, or baseline signal-stretch (BSS) as desribed in A. J. Croxford, J. Moll, P. D. Wilcox, and J. E. Michaels, "Efficient temperature compensation strategies for guided wave structural health monitoring," *Ultrasonics,* 50 (4-5), pp. 517-528 (2010), incorporated herein by reference, and the equation above is not intended to limit the interpretation of how a scattered signal may be obtained.

Figure 6:
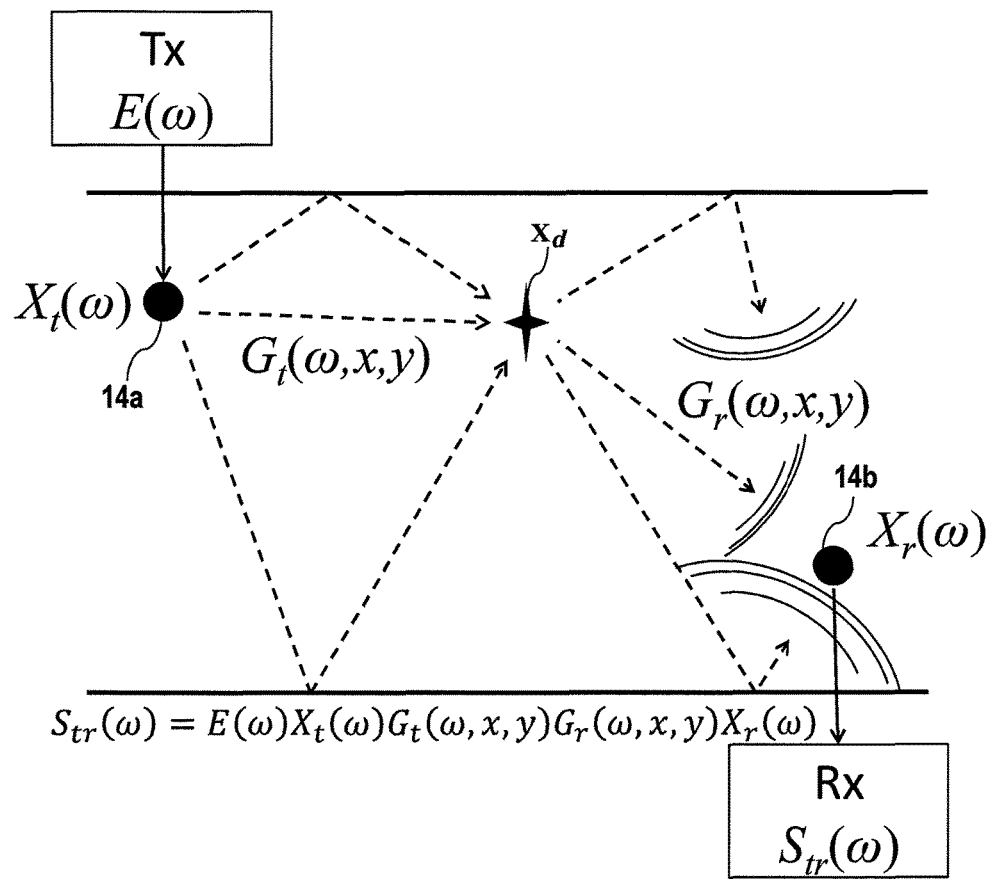
FIG. 6 illustrates signal components, including multiple propagation paths, for a scattered signal when damage is present in a structure.

In step 210, in the unknown state, the baseline data $B_{tr}(\omega)$ and the test data $T_{tr}(\omega)$ are combined to compute a scattered impulse response $H_{tr}(\omega)$. If a scatterer is present in the structure 12 when test data $T_{tr}(\omega)$ is collected that was not present during collection of the baseline data $B_{tr}(\omega)$, then the scattered signal will contain a large number of overlapping echoes and reverberations. Each echo will correspond, as shown in FIG. 6, to a propagation path from transmitter 14a, to scatterer $x_d$, to receiver 14b and may additionally include one or more interactions with the geometric features of the structure. According to an embodiment, the scattered signal can be interpreted as the output of a multi-path system in which a single input signal results in a series of overlapping echoes:

$$S_{tr}(\omega) = E(\omega) H_{tr}(\omega),$$

where $H_{tr}(\omega)$ is referred to herein as the "scattered impulse response" and is a function of both the transducer pair, tr, and an unknown scatterer location, $x_d$. In this context, the scattered impulse response corresponds to the impulse response of the structure 12 under the condition that each of the multi-path echoes includes at least one interaction with a scatterer located at $x_d$.

Mathematically, the scattered impulse response $H_{tr}(\omega)$ is expressed as follows for a point-like scatterer:

$$H_{tr}(\omega) = X_t(\omega) G_t(\omega, x_d) G_r(\omega, x_d) X_r(\omega), \quad (2)$$

where $X_t(\omega)$ and $X_r(\omega)$ are the transducer transfer functions for transducers t and r, respectively, and $G_t(\omega, x_d)$ and $G_r(\omega, x_d)$ are the Green's functions that describe the multi-path guided wave propagation between transducers t and r, respectively, and the unknown defect location $X_d$. The scattered impulse response $H_{tr}(\omega)$ is also dependent on the scattering behavior of the defect. For readability, however, this embodiment will address only a point-like, or uniform, scattering defect. An additional embodiment that accounts for directional scattering is described in further detail below.

The scattered impulse response can be computed (step 210) through deconvolution:

$$H_{tr}(\omega) = \frac{S_{tr}(\omega)}{E(\omega)}. \quad (3)$$

In the above equation, the actual defect location, $x_d$, is unknown. To find $x_d$, one or more estimates of the scattered impulse response $H_{tr}(\omega)$ can be estimated in step 120 for any of the locations of interest, $x_i$, using data collected prior to the presence of any defect or damage. To illustrate, notice that the $V_z(\omega, x_i)$ measurements, taken in a known state (step 110), can be combined to estimate the scattered impulse response at each location of interest, $x_i$ (step 120):

$$\hat{H}_{tr}(\omega, x_i) = \frac{V_t(\omega, x_i) V_r(\omega, x_i)}{E^2(\omega) L^2(\omega)}. \quad (4)$$

For example, note that based on Eq. (1)-(4): $\hat{H}_{tr}(\omega, x_i) = H_{tr}(\omega)$ when $x_i = x_d$. Eq. (4), therefore, describes a method to estimate a combination of the transducer transfer functions for each of the two transducers, $X_t(\omega)$ and $X_r(\omega)$, and the Green's function between two transducers corresponding to the case when a point-like scatterer is located at a spatial point of interest. Note that the tth and rth transducers may be identical. For example, a single transducer may be used to both excite waves and record data.

To facilitate damage detection and localization, a quantitative comparison between the scattered impulse response, $H_{tr}(\omega)$, and the estimated scattered impulse responses, $\hat{H}_{tr}(\omega, x_i)$, can be made (step 300). This comparison may be implemented via any number of different mechanisms, including, but not limited to, cross-correlation, deconvolution, weighted cross-correlation, or regularized deconvolution.

To illustrate one preferred embodiment of step 300, Wiener deconvolution will be used to perform the comparison. Weiner deconvolution for the estimated scattered impulse response at location $x_i$ using transducer pair tr is computed as:

$$D_{tr}(\omega, x_i) = \frac{H_{tr}(\omega) \hat{H}_{tr}^*(\omega, x_i)}{\hat{H}_{tr}(\omega, x_i) \hat{H}_{tr}^*(\omega, x_i) + \sigma} \quad (5)$$

where $D_{tr}(\omega, x_i)$ is the Weiner deconvolved signal and $\sigma$ is a regularization parameter. Since Weiner deconvolution can cause a substantial distortion of the signal, it is important to anticipate what a Weiner deconvolved signal will look like if $\hat{H}_{tr}(\omega, x_i)$ exactly matches $H_{tr}(\omega)$. The anticipated Weiner deconvolved signal is computed by substituting $\hat{H}_{tr}(\omega, x_i)$ for $H_{tr}(\omega)$ in Eq. (5), producing:

$$A_{tr}(\omega, x_i) = \frac{|\hat{H}_{tr}(\omega_i, x_i)|^2}{|\hat{H}_{tr}(\omega, x_i)|^2 + \delta}. \quad (6)$$

As with the Weiner deconvolved signal, $D_{tr}(\omega,x_i)$, the anticipated Weiner deconvolved signal described in Eq. (6) depends upon both the transducer pair, tr, as well as the location, $x_i$.

The quantitative comparison (step 300) for this embodiment may be performed through an inner product operation. The inner product is computed using normalized versions of both the Weiner deconvolved signals and anticipated signals:

$$M_{tr}(x_i) = \left\langle \frac{A_{tr}(\omega, x_i)}{\|A_{tr}(\omega, x_i)\|}, \frac{D_{tr}(\omega, x_i)}{\|D_{tr}(\omega, x_i)\|} \right\rangle \quad (7)$$

Eq. (7) produces a single quantitative comparison between the anticipated signal and Weiner deconvolved signal for each transmitter-receiver pair. While it is not a prerequisite for the quantitative comparison to produce values within the range of ±1, the normalization precludes large or small magnitude $A_{tr}(\omega,x_i)$ or $D_{tr}(\omega,x_i)$ from negatively affecting the results.

The transmitter-receiver comparison results, $M_{tr}(x_i)$, are then combined to produce a single set of values that can be used to perform damage detection and localization (step 310). Several different methods are available to perform this operation. An effective technique involves a weighted summation of the $M_{tr}(x_i)$ values:

$$P(x_i) = \left| \sum_{tr} \alpha_{tr} M_{tr}(x_i) \right|^2, \quad (8)$$

with $\alpha_{tr}$ representing the weighting coefficient that should be applied to each transducer pair and $\Sigma_{tr}$ indicating a summation over all transducer pairs. The weighting coefficient may be uniform over all transducer pairs, or may be obtained through any number of additional techniques, including adaptive methods such as maximum likelihood or minimum variance as disclosed in, for example, J. S. Hall and J. E. Michaels, "Minimum variance ultrasonic imaging applied to an in situ sparse guided wave array," *IEEE Trans. Ultrason., Ferroelectr., Freq. Control*, 57 (10), pp. 2311-2323 (2010) and J. S. Hall and J. E. Michaels, "Computational efficiency of ultrasonic guided wave imaging algorithms," *IEEE Trans. Ultrason., Ferroelectr., Freq. Control*, 58 (1), pp. 244-248 (2011), both of which are hereby incorporated by reference. The values computed in Eq. (8) represent the relative likelihood of a defect at each spatial point of interest. These values can either be presented as an image to facilitate interpretation and localization, or interpreted directly for automated damage detection and localization.

Figure 7:
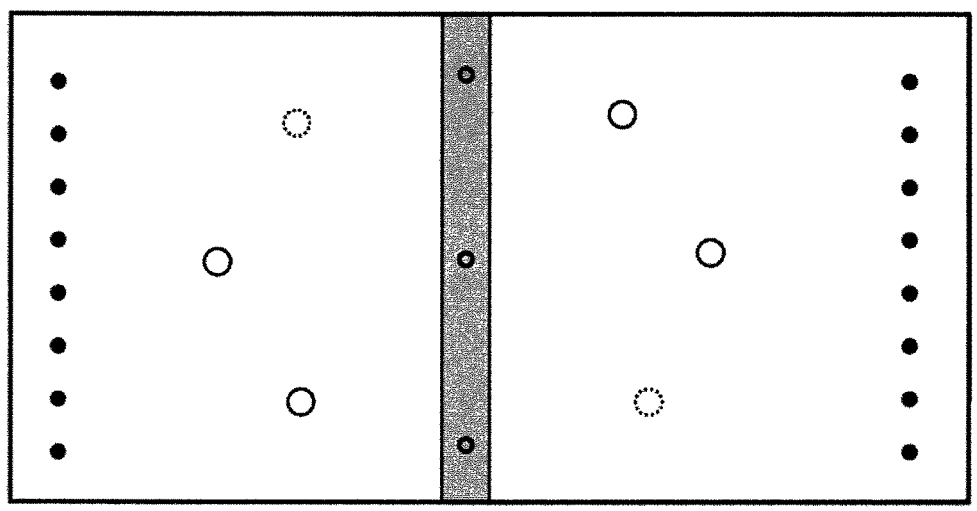
FIG. 7 depicts an experimental specimen comprised of six transducers, sixteen through-holes, three fasteners, and a doubler.

To illustrate the generation of an image using Eq. (8), consider the example case of a 292×597×3.175 mm aluminum 6061 plate shown in FIG. 7. The plate has a bonded doubler, three fasteners, and sixteen through-holes. The relatively small size of the structure serves to create a large number of edge reflections. Six piezoelectric transducers, with a resonant frequency of 300 kHz, were permanently attached to the plate in an approximately circular pattern, with three on each side of the doubler. Of the six transducers, only four were used for data collection. The $V_t(\omega,\vec{x})$ measurements were collected on a 14×10 mm grid using a SLV, producing 626 separate signals for each transducer. A 100 kHz 3-cycle Hann-windowed toneburst was used as the source excitation for all data acquisition. Simulated damage was introduced using two 8 mm diameter magnets attached to opposite sides of the plate.

Figure 8:
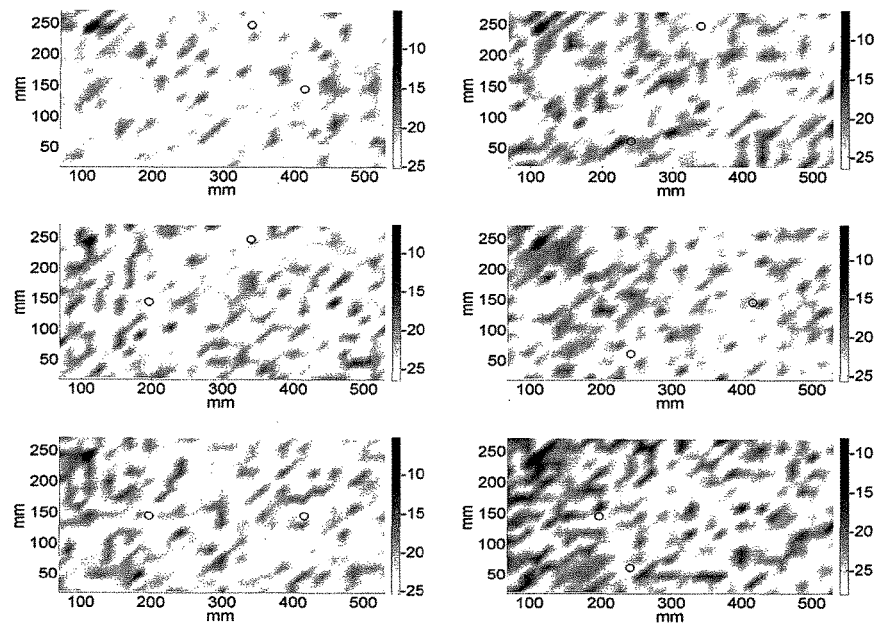
FIG. 8 shows six images generated using different combinations of two transducers on the experimental specimen of FIG. 7.

FIG. 8 provides exemplary imaging results computed with Eq. (8) when only one transducer pair is used to detect a simulated defect located in the upper left of the complex structure. Each subplot of FIG. 8 depicts the two transducers used to generate the image as open circles and displays the $P(x_i)$ value for each pixel location on a dB gray-scale. While there is substantial noise present in each image, this figure illustrates that even a single transducer pair in operation in accordance with an embodiment of the system of method of the invention is able to produce images that correctly identify the defect location.

Figure 9:
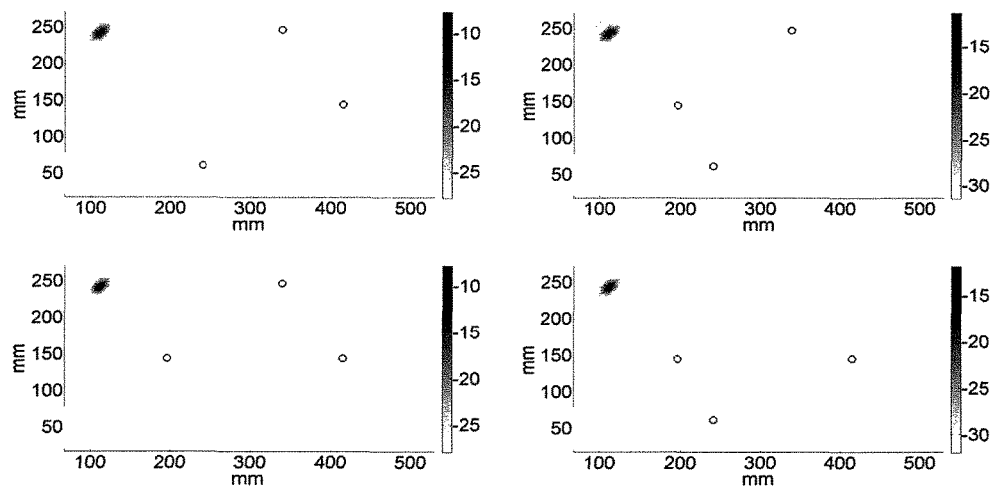
FIG. 9 shows four images generated using different combinations of three transducers on the experimental specimen of FIG. 7.

FIG. 9 depicts imaging results computed with Eq. (8) when three transducers (and thus, three transducer pairs) are used to detect the same simulated defect located in the upper left of the complex structure. Since more than one transducer pair is employed, the weighting coefficients of Eq. (8) must be set. For this example, minimum variance distortionless response (an adaptive algorithm) was used to compute the weighting coefficients. For each of the three transducer arrangements depicted in FIG. 9, one can see that there is dramatic improvement with the addition of transducers. The dramatic improvement of FIG. 9 over FIG. 8 is largely due to (1) the independence of imaging artifacts visible in FIG. 8 and (2) the use of adaptive weighting coefficients.

Eq. (2) above inherently assumes that all incident waves will be scattered uniformly from a defect at location $x_i$. This has been found to be a reasonable assumption for small defects, however, larger defects can be highly directional. An additional, more general embodiment is presented here to illustrate how the invention can be expanded to accommodate multi-mode propagation, mode conversion, and directional scatterers. There are two primary benefits to incorporating this information into the present invention: (1) the additional information improves the ability of the invention to detect and locate scatterers and (2) it enables the invention to perform defect characterization.

Figure 10:
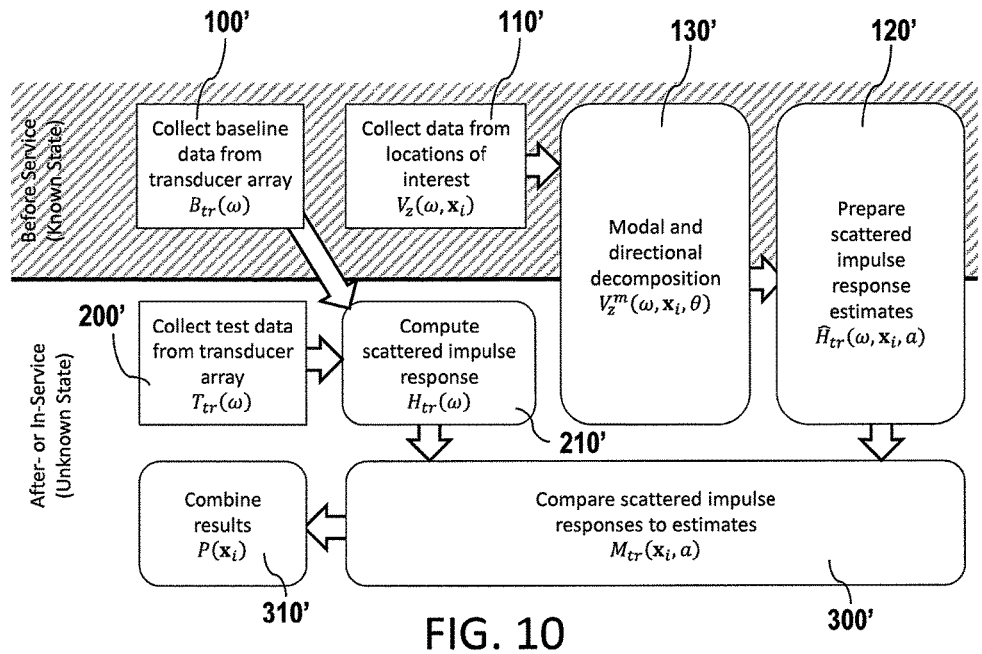
FIG. 10 illustrates a flow chart depicting a method of detecting, localizing, and characterizing a defect at one or more spatial points of interest on a structure for the case of multi-mode propagation, mode conversion, and directional scatterers according to an embodiment.
Figure 11:
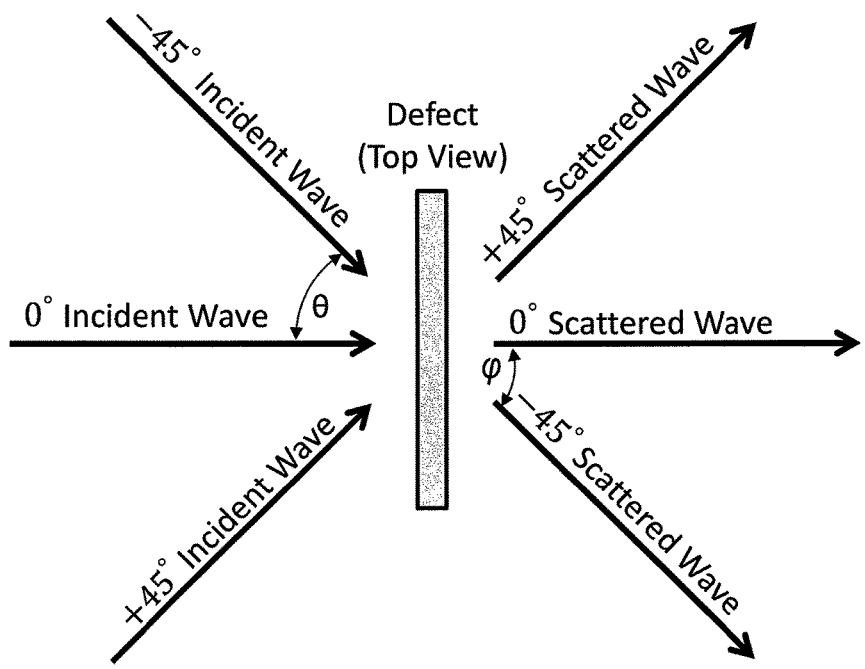
FIG. 11 illustrates a top schematic view of a defect having sufficient size and shape to define a directional scatterer according to an embodiment.

FIG. 10 illustrates a flow chart depicting a method of detecting, localizing, and characterizing a defect at one or more spatial points of interest on a structure 12 for the case of multi-mode propagation, mode conversion, and directional scatterers according to an embodiment. FIG. 11 illustrates a top schematic view of a defect having sufficient size and shape to define a directional scatterer according to an embodiment. FIG. 10 is analogous to FIG. 2 except that it includes a step related to modal and directional decomposition. The embodiment shown in FIG. 2 is a simplified case of the embodiment shown in FIG. 10.

In order to accommodate multi-mode propagation and directional scattering, the $V_z(\omega,x_i)$ data must be decomposed into both directional and modal components (step 130') as shown in FIG. 10. The decomposition method is ancillary to the purpose of this document, but it can be performed through physical selectivity, e.g. mode or directional specific sensors, or through advanced signal processing methods, e.g. spatial-domain filtering techniques as disclosed, for example, in T. E. Michaels, J. E. Michaels, and M. Ruzzene, "Frequency-wavenumber domain analysis of guided wavefields," *Ultrasonics*, 51 (4), pp. 452-466 (2011), hereby incorporated by reference. Regardless of the decomposition method, the $V_z(\omega, x_i)$ data is assumed from this point on to be decomposed into $V_z^m(\omega, x_i, \theta)$ components, where $\theta$ corresponds to the propagation direction and m indicates the propagation mode.

The following equation expands Eq. (4) to accommodate directional scattering information for a single propagating mode, $S_0$ (step 120'):

$$\hat{H}_{tr}(\omega, x_i, j) = \qquad (9)$$

$$\frac{\int_0^{2\pi} \int_0^{2\pi} V_t^{S_0}(\omega, x_i, \theta) Z_j^{S_0 S_0}(\omega, \theta, \varphi) V_r^{S_0}(\omega, x_i, \varphi + \pi) d\theta d\varphi}{E^2(\omega) L^2(\omega)}$$

where $\hat{H}_{tr}(\omega, x_i, j)$ is the estimated scattered signal that will result when the jth potential defect is located at $x_i$ and $Z_j^{S_0 S_0}(\omega, \theta, \varphi)$ provides scattering information about the jth potential defect for an $S_0$ wave incident at angle $\theta$ and scattered as an $S_0$ wave at angle $\varphi$. FIG. 11 graphically illustrates how the incident and scattered angles are defined. The addition of $\pi$ in the $V_r^{S_0}(\omega, x_i, \theta+\pi)$ term is required to account for the angle definition. Estimates of the frequency dependent scattering pattern, $Z_h^{S_0 S_0}(\omega, \theta, \varphi)$, can be obtained via closed form solutions, finite element modeling, or experimental methods that would be understood by one of skill in the art and, accordingly, are not explained further herein.

The scattered impulse response model can be further expanded to incorporate multi-mode propagation and mode conversion information. For this example, consider a scatterer in which an incident $S_0$ mode produces both scattered $S_0$ and scattered $A_0$ waves. In this case, the scattering function will need to describe both the $S_0$ to $S_0$ scattering, $Z_j^{S_0 S_0}(\omega, \theta, \varphi)$, $S_0$ to $A_0$ scattering, $Z_j^{S_0 A_0}(\omega, \theta, \varphi)$, $A_0$ to $S_0$ scattering, $Z_j^{A_0 S_0}(\omega, \theta, \varphi)$, and $A_0$ to $A_0$ scattering, $Z_j^{A_0 A_0}(\omega, \theta, \varphi)$. This information can be incorporated into the previous equation (step 120') as:

$$\hat{H}_{tr}(\omega, x_i, j) = \frac{\sum_{m=S_0, A_0} \sum_{n=S_0, A_0} \int_0^{2\pi} \int_0^{2\pi} V_t^m(\omega, x_i, \theta) Z_j^{mn}(\omega, \theta, \varphi) V_r^n(\omega, x_i, \varphi + \pi) d\theta d\varphi}{E^2(\omega) L^2(\omega)} \qquad (10)$$

The model can be further expanded to accommodate higher modes, e.g. $S_1, A_1, S_2$, etc., however, the additional notation is foregone here in the interest of space and simplicity.

It is important to note that Eq. (4) is simply a degenerate case of Eq. (9), where $Z_j^{S_0 S_0}(\omega, \theta, \varphi)=1$ for all $\theta$ and $\varphi$. Similarly, Eq. (9) is a degenerate case of Eq. (10), where the summation terms with $n=A_0$ or $m=A_0$ are considered to be negligible. As such, the most general form of the estimated scattered impulse response, $\hat{H}_{tr}(\omega, x_i, j)$ is shown in Eq. (10).

Defect-specific scattered impulse response estimates, $\hat{H}_{tr}(\omega, x_i, j)$, can be quantitatively compared to the scattered impulse responses, $H_{tr}(\omega)$ in the same manner as shown in Eq. (5)-(7) (step 300'). The difference between step 300' and step 300 is that each of the calculation outputs will be defect-specific, e.g. $A_{tr}(\omega, x_i, j)$ or $D_{tr}(\omega, x_i, j)$, and $M_{tr}(x_i, j)$.

Defect detection and localization with defect-specific comparison values can be performed in a variety of methods (step 310'). In an embodiment, the computation of $P(x_i, j)$ for each potential defect can be performed in a manner similar to Eq. (8), $$P(x_i, j) = \left| \sum_{tr} \alpha_{tr} M_{tr}(x_i, j) \right|^2, \qquad (11)$$

with the addition of a max operation:

$$P(x_i) = \max\{P(x_i, j) \text{ for all } j\}. \qquad (12)$$

The above formulation will produce a large magnitude $P(x_i)$ when one of the potential defects is located at $x_i$. As before, the values computed in Eq. (12) can either be presented as an image to facilitate interpretation and localization, or interpreted directly for automated damage detection and localization. Damage characterization is performed by identifying the most likely potential defect at any given location, $J(x_i)$, which can be identified as:

$$J(x_i) = \max_j P(x_i, j). \qquad (13)$$

Figure 12:
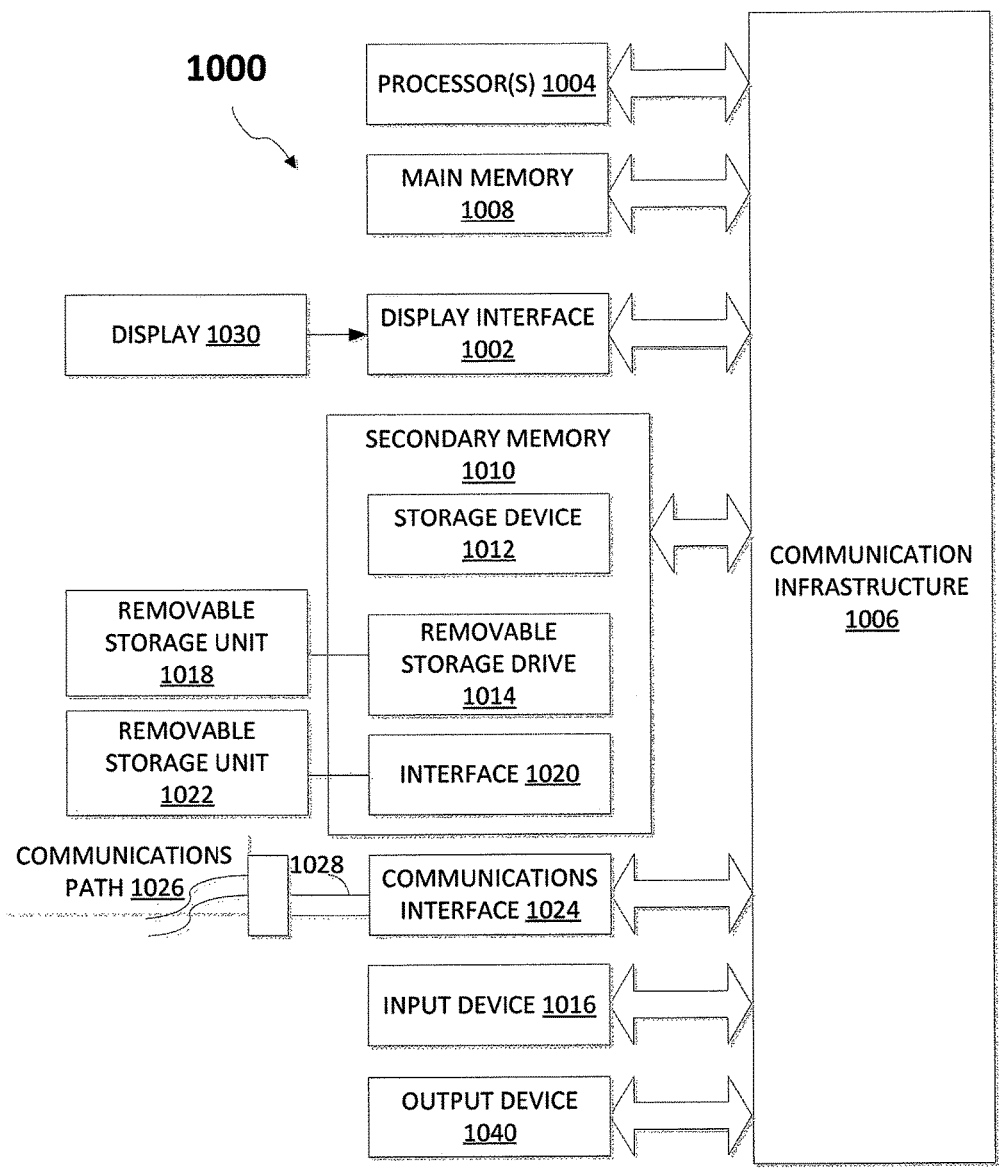
FIG. 12 depicts an illustrative embodiment of a computer system that may be used in association with, in connection with, and/or in place of, e.g., but not limited to, any of the foregoing components and/or systems according to an embodiment of the invention.

FIG. 12 depicts an illustrative embodiment of a computer system 1000 that may be used in association with, in connection with, and/or in place of, e.g., but not limited to, any of the foregoing components and/or systems. The system 10 and method of detecting, localizing, and characterizing a defect at one or more spatial points of interest on a structure may be implemented with one or more such computer systems 1000.

The present embodiments (or any part(s) or function(s) thereof) may be implemented using hardware, software, firmware, or a combination thereof and may be implemented in one or more computer systems or other processing systems. In an embodiment, the invention may be directed toward one or more computer systems capable of carrying out the functionality described herein. An example of a computer system 1000 is shown in FIG. 12, which depicts a block diagram of an exemplary computer system which may be useful for implementing the present invention. Specifically, FIG. 12 illustrates an example computer 1000, which in an exemplary embodiment may be, e.g., (but not limited to) a personal computer (PC) system running an operating system such as, e.g., (but not limited to) WINDOWS MOBILE™ for POCKET PC, or MICROSOFT® WINDOWS® NT/98/2000/XP/CE/7/VISTA, etc. available from MICROSOFT® Corporation of Redmond, Wash., U.S.A., SOLARIS® from SUN® Microsystems of Santa Clara, Calif., U.S.A., OS/2 from IBM® Corporation of Armonk, N.Y., U.S.A., Mac/OS from APPLE® Corporation of Cupertino, Calif., U.S.A., etc., or any of various versions of UNIX® (a trademark of the Open Group of San Francisco, Calif., USA) including, e.g., LINUX®, HPUX®, IBM AIX®, and SCO/UNIX®, etc. However, the invention may not be limited to these platforms. Instead, the invention may be implemented on any appropriate computer system running any appropriate operating system. In one exemplary embodiment, the present invention may be implemented on a computer system operating as discussed herein. Other components of the invention, such as, e.g., (but not limited to) a computing device, a communications device, a telephone, a personal digital assistant (PDA), a personal computer (PC), a handheld PC, client workstations, thin clients, thick clients, proxy servers, network communication servers, remote access devices, client computers, server computers, routers, web servers, data, media, audio, video, telephony or streaming technology servers, etc., may also be implemented using a computer such as that shown in FIG. 12.

The computer system 1000 may include one or more processors, such as, e.g., but not limited to, processor(s) 1004. The processor(s) 1004 may be connected to a communication infrastructure 1006 (e.g., but not limited to, a communications bus, cross-over bar, or network, etc.). Various exemplary software embodiments may be described in terms of this exemplary computer system. After reading this description, it will become apparent to a person skilled in the relevant art(s) how to implement the invention using other computer systems and/or architectures.

Computer system 1000 may include a display interface 1002 that may forward, e.g., but not limited to, graphics, text, and other data, etc., from the communication infrastructure 1006 (or from a frame buffer, etc., not shown) for display on the display unit 1030.

The computer system 1000 may also include, e.g., but may not be limited to, a main memory 1008, random access memory (RAM), and a secondary memory 1010, etc. The secondary memory 1010 may include, for example, (but may not be limited to) one or more hard disk or solid state drives 1012 and/or a removable storage drive 1014, representing a floppy diskette drive, a magnetic tape drive, an optical disk drive, a magneto-optical disk drive, a compact disk drive CD-ROM, a digital versatile disk (DVD), a write once read many (WORM) device, a flash memory device, etc. The removable storage drive 1014 may, e.g., but not limited to, read from and/or write to a remote or removable storage unit 1018 in a well-known manner. Removable storage unit 1018, also called a program storage device or a computer program product, may represent, e.g., but not limited to, a floppy disk, a magnetic tape, an optical disk, a magneto-optical disk, a compact disk, a flash memory device, etc. which may be read from and written to by removable storage drive 1014. As will be appreciated, the removable storage unit 1018 may include a computer usable storage medium having stored therein computer software and/or data.

In alternative exemplary embodiments, secondary memory 1010 may include other similar devices for allowing computer programs or other instructions to be loaded into computer system 1000. Such devices may include, for example, a removable storage unit 1022 and an interface 1020. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units 1022 and interfaces 1020, which may allow software and data to be transferred from the removable storage unit 1022 to computer system 1000.

Computer 1000 may also include an input device 1016 such as, e.g., (but not limited to) a mouse or other pointing device such as a digitizer, a keyboard or other data entry device (none of which are labeled), and/or a touchscreen integrated with display 1030, etc.

Computer 1000 may also include output devices 1040, such as, e.g., (but not limited to) display 1030, and display interface 1002. Computer 1000 may include input/output (I/O) devices such as, e.g., (but not limited to) communications interface 1024, cable 1028 and communications path 1026, etc. These devices may include, e.g., but not limited to, a network interface card, and modems (neither are labeled). Communications interface 1024 may allow software and data to be transferred between computer system 1000 and external devices. Examples of communications interface 1024 may include, e.g., but may not be limited to, a modem, a network interface (such as, e.g., an Ethernet card), a communications port, a Personal Computer Memory Card International Association (PCMCIA) slot and card, a transceiver, a global positioning system receiver, etc. Software and data transferred via communications interface 1024 may be in the form of signals 1028 which may be electronic, electromagnetic, optical or other signals capable of being received by communications interface 1024. These signals 1028 may be provided to communications interface 1024 via, e.g., but not limited to, a communications path 1026 (e.g., but not limited to, a channel). This channel 1026 may carry signals 1028, which may include, e.g., but not limited to, propagated signals, and may be implemented using, e.g., but not limited to, wire or cable, fiber optics, a telephone line, a cellular link, an radio frequency (RF) link and other communications channels, etc.

In this document, the terms "computer program medium" and "computer readable medium" may be used to generally refer to non-transitory media such as, e.g., but not limited to removable storage drive 1014, a hard disk installed in hard disk drive, a solid state drive, and/or other storage device 1012, etc. These computer program products may provide software to computer system 1000. The invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, variables, symbols, characters, terms, numbers or the like. It should be understood, however, that all of these and similar terms are to be associated with the appropriate physical quantities and are merely convenient labels applied to these quantities.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses and/or devices for performing the operations herein. An apparatus may be specially constructed for the desired purposes, or it may comprise a general purpose device selectively activated or reconfigured by a program stored in the device.

Embodiments of the invention may be implemented in one or a combination of hardware, firmware, and software. Embodiments of the invention may also be implemented as instructions stored on a machine-readable medium, which may be read and executed by a computing platform to perform the operations described herein. A machine-readable medium may include any tangible, non-transitory mechanism for storing or transmitting information in a form readable by a machine (e.g., a computer). For example, an exemplary machine-readable storage medium may include, e.g., but not limited to, read only memory (ROM); random access memory (RAM); magnetic disk storage media; optical storage media; magneto-optical storage media; and flash memory devices.

Computer programs (also called computer control logic), may include object oriented computer programs, and may be stored in main memory 1008 and/or the secondary memory 1010 and/or removable storage drive 1014, removable storage unit 1018, removable storage unit 1022, also called computer program products. Such computer programs, when executed, may enable the computer system 1000 to perform the features of the inventive embodiments discussed herein. In particular, the computer programs, when executed, may enable the processor or processors 1004 to perform steps for detecting, localizing, and characterizing a defect at one or more spatial points of interest on a structure and/or for computing an estimated scattered impulse response at the one or more spatial points of interest based on collected data. For example, the processor or processors 1004 may output signals to excite one or more of the plurality of transducers 14 on the structure 12. Alternatively, or in addition, the processor or processors 1004 may receive and process signals from one or more of the plurality of transducers 14 on the structure 12 and/or from the movable transducer 20 according to the embodiments described herein.

In another exemplary embodiment, the invention may be directed to a computer program product comprising a computer readable medium having control logic (computer software) stored therein. The control logic, when executed by the processor 1004, may cause the processor 1004 to perform the functions of the invention as described herein. In another exemplary embodiment where the invention may be implemented using software, the software may be stored in a computer program product and loaded into computer system 1000 using, e.g., but not limited to, removable storage drive 1014, hard drive 1012 or communications interface 1024, etc. The control logic (software), when executed by the processor 1004, may cause the processor 1004 to perform the functions of the invention as described herein. The computer software may run as a standalone software application program running atop an operating system, may be integrated into the operating system, or may be integrated into another software program.

In yet another embodiment, the invention may be implemented primarily in hardware using, for example, but not limited to, hardware components such as one or more application specific integrated circuits (ASICs), field programmable gate-arrays (FPGAs), or other devices, etc. Implementation of a hardware device capable of performing the functions described herein will be apparent to persons skilled in the relevant art(s).

In another exemplary embodiment, the invention may be implemented primarily in firmware.

In yet another exemplary embodiment, the invention may be implemented using a combination of any of, e.g., but not limited to, hardware, firmware, and software, etc.

The exemplary embodiment of the present invention makes reference to, e.g., but not limited to, communications links, wired, and/or wireless networks. Wired networks may include any of a wide variety of well-known wired connections for coupling sensors, processors, and other devices together. A brief discussion of various exemplary wireless network technologies that may be used to implement the embodiments of the present invention now are discussed. The examples are non-limiting. Exemplary wireless network types may include, e.g., but not limited to, code division multiple access (CDMA), spread spectrum wireless, orthogonal frequency division multiplexing (OFDM), 1G, 2G, 3G, 4G wireless, Bluetooth, Infrared Data Association (IrDA—a standard method for devices to communicate using infrared light pulses), shared wireless access protocol (SWAP), "wireless fidelity" (Wi-Fi), WIMAX, and other IEEE standard 802.11-compliant wireless local area network (LAN), 802.16-compliant wide area network (WAN), and ultrawideband (UWB) networks, etc.

According to an embodiment, the methods set forth herein may be performed by one or more computer processor(s) adapted to process program logic, which may be embodied on a computer accessible storage medium, which when such program logic is executed on the exemplary one or more processor(s) may perform such steps as set forth in the methods.

While various embodiments of the present invention have been described above, it should be understood that they have been presented by way of example only, and not limitation. Although the foregoing description is directed to example embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A method of estimating and storing for subsequent use after a structure has transitioned to an unknown state one or more estimated scattered impulse responses corresponding to one or more spatial points of interest on the structure, wherein an estimated scattered impulse response represents an estimate of the impulse response of the structure under the condition that each of the multi-path echoes includes at least one interaction with a scatterer located at the corresponding spatial point of interest, comprising:

collecting data at one or more spatial points of interest on the structure when the structure is in a known state using a movable transducer, wherein collecting data includes individually exciting at least one transducer physically affixed to the structure with a known excitation function and recording measurements at the one or more spatial points of interest with the movable transducer wherein each collected data corresponds to exactly one spatial point of interest and contains one or more multi-path echoes corresponding to a path originating at the one or more excitation transducers, terminating at the corresponding spatial point of interest, and interacting with one or more features of the structure;

computing one or more estimated scattered impulse responses, each corresponding to exactly one of the one or more spatial points of interest by combining two or more of the collected data corresponding to the same spatial point of interest; and storing said estimated scattered impulse responses for subsequent use after the structure has transitioned to an unknown state.

2. The method according to claim 1, wherein the computing one or more estimated scattered impulse responses includes decomposing the collected data into one or more data sets having mode and/or directional specificity.

3. The method according to claim 1, wherein the movable transducer is configured to obtain data with mode and/or directional specificity.

4. A method of detecting, localizing, and characterizing a defect at one or more spatial points of interest on a structure, after the structure has transitioned to an unknown state, comprising:
 collecting first data when the structure is in a known state from at least one transducer physically affixed to the structure, wherein the collecting first data includes individually exciting one or more of the at least one transducer with a known excitation function and recording the signals received from one or more of the at least one transducer;
 storing said first data for subsequent, non-contemporaneous use after the structure has transitioned to an unknown state;
 collecting second data from the at least one transducer physically affixed to the structure after the structure has transitioned to an unknown state, wherein the collecting second data includes individually exciting one or more of the at least one transducer with a known excitation function and recording the signals received from one or more of the at least one transducer;
 retrieving said first data collected when the structure is in a known state;
 computing a scattered impulse response based on the retrieved first data and the collected second data;
 retrieving one or more previously estimated scattered impulse responses, wherein each estimated scattered impulse response corresponds to exactly one of the one or more spatial points of interest;
 comparing the retrieved estimated scattered impulse responses with the computed scattered impulse response to generate comparison results; and
 combining the generated comparison results to detect, localize, and characterize a defect at the one or more spatial points of interest on the structure.

5. The method according to claim 4, wherein the at least one transducer physically affixed to the structure comprises a plurality of transducers spaced from one another on the structure,
 wherein the collecting first data includes individually exciting one or more of the plurality of transducers with a known excitation function and recording the signals received from one or more of the transducers, and
 wherein the collecting second data includes individually exciting one or more of the plurality of transducers with a known excitation function and recording the signals received from one or more of the transducers.

6. The method according to claim 4, wherein the computing the scattered impulse response comprises isolating the differences between the collected second data and the retrieved first data.

7. The method according to claim 4, wherein the comparing the retrieved estimated scattered impulse responses with the computed scattered impulse response to generate comparison results comprises
 utilizing deconvolution, cross-correlation, weighted cross-correlation, regularized deconvolution, Weiner deconvolution, or other mathematically equivalent operation to generate a unique comparison result for each respective pair of transducers.

8. The method according to claim 7, wherein the unique comparison result for each respective pair of transducers is obtained by comparing the results from deconvolution, cross-correlation, weighted cross-correlation, regularized deconvolution, Weiner deconvolution or other mathematically equivalent operation with anticipated values through an inner product, correlation, or other mathematically equivalent operation.

9. The method according to claim 4, wherein the combining the generated comparison results comprises
 calculating a weighted summation of the unique comparison results for each respective pair of transducers.

10. The method according to claim 9, wherein the calculating a weighted summation includes weighting coefficients determined through an adaptive algorithm or process.

11. A system for detecting, localizing, and characterizing a defect at one or more spatial points of interest on a structure, comprising:
 at least one transducer physically affixed to the structure, wherein the at least one transducer is configured to be excited according to a known excitation function, and wherein the at least one transducer is configured to record a signal received from excitation of one or more of the at least one transducer;
 a storage device containing one or more estimated scattered impulse responses for each of the one or more spatial points of interest on the structure; and
 a processor coupled to the at least one transducer, wherein the processor is configured to:
  collect first data when the structure is in a known state by individually exciting one or more of the at least one transducer with a known excitation function and processing the signals received from one or more of the at least one transducer;
  store the first data for subsequent, non-contemporaneous use after the structure has transitioned to an unknown state;
  subsequently collect second data after the structure has transitioned to an unknown state by individually exciting one or more of the at least one transducer with a known excitation function and processing the signals received from one or more of the at least one transducer;
  compute a scattered impulse response based on the stored first data and the collected second data;
  compare the computed scattered impulse response with the stored estimated scattered impulse responses to generate comparison results; and
  combine the generated comparison results to detect, localize, and characterize a defect at the one or more spatial points of interest on the structure.

12. The system of claim 11, wherein the at least one transducer physically affixed to the structure comprises a plurality of transducers spaced from one another on the structure, and wherein one or more of the plurality of transducers are configured to record a signal received from excitation of one or more of the plurality of transducers.

13. The system of claim 11, further comprising:
 a movable transducer configured to record measurements taken at the one or more spatial points of interest during individual excitement of the at least one transducer, wherein the processor is configured to:
  collect data when the structure is in a known state by receiving and processing measurements taken with the movable transducer from each of the one or more spatial points of interest during individual excitement of the at least one transducer;

compute one or more estimated scattered impulse responses corresponding to each of the one or more spatial points of interest based on the collected data; and store said estimated scattered impulse responses for use after the structure has transitioned to an unknown state.

14. The system of claim 13, wherein the movable transducer is configured to record mode-specific and/or directional measurements taken at the one or more spatial points of interest.

15. The system of claim 13, wherein the processor is configured to decompose the data recorded from the movable transducer at the one or more spatial points of interest into mode-specific and/or directional components.

16. The system of claim 11, wherein the processor is configured to use deconvolution, cross-correlation, weighted cross-correlation, regularized deconvolution, Weiner deconvolution, or a mathematically equivalent operation to compare the scattered impulse response with an estimated scattered impulse response.

17. The system of claim 16, wherein the processor is configured to use an anticipated function or value based on the estimates of the scattered impulse response to perform structural interrogation.

18. A method of actively detecting, localizing, and characterizing a defect at one or more spatial points of interest on a structure, comprising:

collecting data at one or more spatial points of interest on the structure while the structure is in a known state using a movable transducer, wherein collecting data includes individually exciting at least one transducer on the structure with a known excitation function and recording measurements at the one or more spatial points of interest with the movable transducer;

computing one or more estimated scattered impulse responses, each corresponding to exactly one of the one or more spatial points of interest based on the collected data;

storing said estimated scattered impulse responses for use after the structure has transitioned to an unknown state;

collecting first data when the structure is in a known state from at least one transducer physically affixed to the structure, wherein the collecting first data includes individually exciting one or more of the at least one transducer with a known excitation function and recording the signal received from one or more of the at least one transducer;

storing said first data for use after the structure has transitioned to an unknown state;

collecting second data from the at least one transducer physically affixed to the structure after the structure has transitioned to an unknown state, wherein the collecting second data includes individually exciting one or more of the at least one transducer with a known excitation function and recording the signal received from one or more of the at least one transducer;

retrieving said first data and computing a scattered impulse response based on the retrieved first data and the collected second data;

retrieving said estimated scattered impulse responses and comparing them with the computed scattered impulse response to generate comparison results; and combining the generated comparison results to detect, localize, and characterize a defect at the one or more spatial points of interest on the structure.

19. The method according to claim 18, wherein computing one or more estimated scattered impulse responses includes decomposing the collected data into one or more data sets with mode and/or directional specificity.

20. The method according to claim 18, wherein the movable transducer is configured to record measurements with mode and/or directional specificity.

UNITED STATES PATENT AND TRADEMARK OFFICE
CERTIFICATE OF CORRECTION

PATENT NO. : 10,126,274 B2
APPLICATION NO. : 14/396373
DATED : November 13, 2018
INVENTOR(S) : James Stroman Hall and Jennifer Emmons Michaels Page 1 of 1

It is certified that error appears in the above-identified patent and that said Letters Patent is hereby corrected as shown below:

On the Title Page

Item [60], insert the following:
--Provisional application No. 61/647,762, filed on May 16, 2012
Provisional application No. 61/756,452, filed on Jan. 24, 2013--

Signed and Sealed this
Twenty-second Day of January, 2019

Andrei Iancu
*Director of the United States Patent and Trademark Office*